(12) United States Patent
Craig et al.

(10) Patent No.: US 7,090,721 B2
(45) Date of Patent: *Aug. 15, 2006

(54) USE OF NANOPARTICLES TO ADJUST REFRACTIVE INDEX OF DENTAL COMPOSITIONS

(75) Inventors: Bradley D. Craig, Cottage Grove, MN (US); Brant U. Kolb, Afton, MN (US); Joel D. Oxman, Minneapolis, MN (US); Robert F. Peez, Germering (DE); Sybille A. Frank, Seefeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/847,803

(22) Filed: May 17, 2004

(65) Prior Publication Data

US 2005/0252414 A1  Nov. 17, 2005

(51) Int. Cl.
*A61K 62/06* (2006.01)

(52) U.S. Cl. .................. 106/35; 523/116; 523/115; 433/228.1

(58) Field of Classification Search .................. None
See application file for complete search history.

(56) References Cited

U.S. PATENT DOCUMENTS

| | | | |
|---|---|---|---|
| 4,209,434 A | 6/1980 | Wilson et al. | |
| 4,259,075 A | 3/1981 | Yamauchi et al. | |
| 4,298,738 A | 11/1981 | Lechtken et al. | |
| 4,324,744 A | 4/1982 | Lechtken et al. | |
| 4,356,296 A | 10/1982 | Griffith et al. | |
| 4,385,109 A | 5/1983 | Lechtken et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,642,126 A | 2/1987 | Zador et al. | |
| 4,652,274 A | 3/1987 | Boettcher et al. | |
| 4,665,217 A | 5/1987 | Reiners et al. | |
| 4,695,251 A | 9/1987 | Randklev | |
| 4,710,523 A | 12/1987 | Lechtken et al. | |
| 4,737,593 A | 4/1988 | Ellrich et al. | |
| 4,752,338 A | 6/1988 | Reiners et al. | |
| 4,772,530 A | 9/1988 | Gottschalk et al. | |
| 4,798,814 A | 1/1989 | Everitt et al. | |
| 4,871,786 A | 10/1989 | Aasen et al. | |
| 4,872,936 A | 10/1989 | Engelbrecht | |
| 4,874,450 A | 10/1989 | Gottschalk | |
| 4,900,697 A | 2/1990 | Akahane et al. | |
| 4,954,414 A | 9/1990 | Adair et al. | |
| 4,954,462 A | 9/1990 | Wood et al. | |
| 5,026,902 A | 6/1991 | Fock et al. | |
| 5,037,579 A | 8/1991 | Matchett | |
| 5,055,372 A | 10/1991 | Shanklin et al. | |
| 5,057,393 A | 10/1991 | Shanklin et al. | |
| 5,063,257 A | 11/1991 | Akahane et al. | |
| 5,076,844 A | 12/1991 | Fock et al. | |
| 5,130,347 A | 7/1992 | Mitra | |
| 5,154,762 A | 10/1992 | Mitra et al. | |
| 5,179,135 A * | 1/1993 | Ellis et al. ................. 523/116 |
| 5,252,122 A | 10/1993 | Arnold | |
| 5,332,429 A | 7/1994 | Mitra et al. | |
| 5,350,782 A | 9/1994 | Sasaki et al. | |
| 5,367,002 A | 11/1994 | Huang et al. | |
| 5,372,796 A | 12/1994 | Wellinghoff | |
| 5,501,727 A | 3/1996 | Wang et al. | |
| 5,520,725 A | 5/1996 | Kato et al. | |
| 5,530,038 A | 6/1996 | Yamamoto et al. | |
| 5,545,676 A | 8/1996 | Palazzotto et al. | |
| 5,609,675 A | 3/1997 | Noritake et al. | |
| 5,670,583 A | 9/1997 | Wellinghoff | |
| 5,694,701 A | 12/1997 | Huelsman et al. | |
| 5,720,805 A | 2/1998 | Wellinghoff et al. | |
| 5,859,089 A | 1/1999 | Qian | |
| 5,883,153 A | 3/1999 | Roberts et al. | |
| 5,925,715 A | 7/1999 | Mitra | |
| 5,980,697 A | 11/1999 | Kolb et al. | |
| 6,194,481 B1 | 2/2001 | Furman et al. | |
| 6,214,101 B1 | 4/2001 | Nakaseko | |
| 6,251,963 B1 | 6/2001 | Kohler et al. | |
| 6,258,974 B1 | 7/2001 | Wellinghoff et al. | |
| 6,262,142 B1 | 7/2001 | Wang et al. | |
| 6,353,040 B1 | 3/2002 | Subelka et al. | |
| 6,376,590 B1 | 4/2002 | Kolb et al. | |
| 6,387,981 B1 | 5/2002 | Zhang et al. | |
| 6,391,286 B1 | 5/2002 | Mitra et al. | |
| 6,410,765 B1 | 6/2002 | Wellinghoff et al. | |
| 6,417,244 B1 | 7/2002 | Wellinghoff et al. | |
| 6,437,019 B1 | 8/2002 | Rusin et al. | |

(Continued)

FOREIGN PATENT DOCUMENTS

DE  19753456 A1  6/1999

(Continued)

OTHER PUBLICATIONS

ASTM D 523-89 (Reapproved 1994) Standard Test Method for Specular Gloss.

(Continued)

*Primary Examiner*—C. Melissa Koslow
(74) *Attorney, Agent, or Firm*—Sean J. Edman

(57) ABSTRACT

The present invention features ionomer compositions containing nanofillers that provide the composition with desirable aesthetic properties (e.g., optical translucency). The compositions can be used in a variety of dental and orthodontic applications, for example, as adhesives, cements, restoratives, coatings and sealants.

42 Claims, No Drawings

U.S. PATENT DOCUMENTS

| | | |
|---|---|---|
| 6,447,907 B1 | 9/2002 | Wolter et al. |
| 6,458,868 B1 | 10/2002 | Okada et al. |
| 6,540,978 B1 | 4/2003 | Margolskee |
| 6,566,413 B1 | 5/2003 | Weinmann et al. |
| 6,572,693 B1 | 6/2003 | Wu et al. |
| 6,620,861 B1 | 9/2003 | Nakatuka et al. |
| 6,624,236 B1 | 9/2003 | Bissinger et al. |
| 6,693,143 B1 | 2/2004 | Pflug |
| 6,695,617 B1 | 2/2004 | Wellinghoff et al. |
| 6,696,507 B1 | 2/2004 | Subelka et al. |
| 6,696,585 B1 | 2/2004 | Wellinghoff et al. |
| 2002/0013382 A1 | 1/2002 | Furman et al. |
| 2002/0193462 A1 | 12/2002 | Angeletakis et al. |
| 2003/0055123 A1 | 3/2003 | Kawashima et al. |
| 2003/0087986 A1 | 5/2003 | Mitra |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0180414 A1 | 9/2003 | Gudas et al. |
| 2003/0181541 A1 | 9/2003 | Wu et al. |
| 2003/0195273 A1 | 10/2003 | Mitra et al. |

FOREIGN PATENT DOCUMENTS

| | | |
|---|---|---|
| EP | 0 173 567 A2 | 3/1986 |
| EP | 0 201 031 A2 | 11/1986 |
| EP | 0 201 778 A1 | 11/1986 |
| EP | 0 201 778 B1 | 11/1988 |
| EP | 0 323 120 A2 | 7/1989 |
| EP | 0 323 120 A3 | 7/1989 |
| EP | 0 201 031 B1 | 8/1989 |
| EP | 0 373 384 B1 | 10/1992 |
| EP | 0 323 120 B1 | 3/1994 |
| EP | 0 373 384 A1 | 6/1996 |
| EP | 0 712 622 B1 | 9/1999 |
| EP | 1 051 961 A1 | 11/2000 |
| EP | 1066813 A | 1/2001 |
| EP | 1 269 968 A1 | 1/2003 |
| GB | 1316129 A | 5/1973 |
| JP | 05 331017 A | 12/1993 |
| JP | 06 321724 A | 11/1994 |
| JP | 2004 067597 A | 3/2004 |
| WO | 00/03688 A1 | 1/2000 |
| WO | 00/03747 A2 | 1/2000 |
| WO | 00/03747 A3 | 1/2000 |
| WO | 00/38619 A2 | 7/2000 |
| WO | 00/38619 A3 | 7/2000 |
| WO | 00/42092 A1 | 7/2000 |
| WO | 01/07444 A1 | 2/2001 |
| WO | 01/30305 A1 | 5/2001 |
| WO | 01/30306 A1 | 5/2001 |
| WO | 01/30307 A1 | 5/2001 |
| WO | 01/92271 A1 | 12/2001 |
| WO | WO 2002/096464 A1 | 12/2002 |
| WO | 03/063804 A1 | 8/2003 |
| WO | WO 2003/063804 | 8/2003 |
| WO | WO 2003/086328 A1 | 11/2003 |
| WO | WO 2004/043343 | 5/2004 |

OTHER PUBLICATIONS

U.S. Appl. No. 10/729,497 entitled "Compositions Including Polymerizable Bis-Phosphonic Acides and Methods," filed Dec. 5, 2003.

U.S. Appl. No. 10/847,782 entitled "Dental Compositions Containing Nanozirconia Fillers," filed May 17, 2004.

U.S. Appl. No. 10/847,781 entitled "Dental Compositions Containing Nanofillers and Related Methods," filed May 17, 2004.

U.S. Appl. No. 10/847,805 entitled "Acid-Reactive Dental Fillers, Compositions, and Methods," filed May 17, 2004.

U.S. Appl. No. 10/327,411 entitled "Dental Compositions Including Enzymes and Methods,"filed Dec. 20, 2002.

Keast Russell S J, et al: "Modifying the Bitterness of Selected Oral Pharmaceuticals with Cation and Anion Series of Salts" Database Biosis 'Online! Biosciences Information Service, Philadelphia, PA US: Jul. 2002 (XP002331214 Database accession No. PREV200200479568 Abstract & Pharmaceutical Research (new York), vol. 19, No. 7, Jul. 2002, pp. 1019-1026, ISNN: 0724-8741.

Stamboulis, et al., "Characterization of the structure of calcium alumino-silicate and calcium fluoro-alumino-silicate glasses by magic angle spinning nuclear magnetic resonance (MAS-NMR)" Journal of Non-Crystalline Solids, Noth-Holland Physics Publishing, Amsterdam, NL, vol. 333, No. 1, Jan. 1, 2004, pp. 01-107, XP004479772, ISSN: 0022-3093 abstract.

\* cited by examiner

US 7,090,721 B2

USE OF NANOPARTICLES TO ADJUST REFRACTIVE INDEX OF DENTAL COMPOSITIONS

FIELD OF THE INVENTION

The present invention relates to hardenable dental and orthodontic compositions filled with nanoparticles that have been selected to effectively match the refractive indices of components of the composition. More specifically, the invention relates to ionomer and resin modified ionomer compositions containing selected nanoparticles that provide the compositions with desirable aesthetic properties, such as optical translucency. The compositions can be used in a variety of applications, for example, as adhesives, cements, restoratives, coatings, and sealants.

BACKGROUND

The restoration of decayed dental structures including caries, decayed dentin or decayed enamel, is often accomplished by the sequential application of a dental adhesive and then a dental material (e.g., a restorative material) to the relevant dental structures. Similar compositions are used in the bonding of orthodontic appliances (generally utilizing an orthodontic adhesive) to a dental structure. Often various pretreatment processes are used to promote the bonding of adhesives to dentin or enamel. Typically, such pretreatment steps include etching with, for example, inorganic or organic acids, followed by priming to improve the bonding between the tooth structure and the overlying adhesive.

A variety of dental and orthodontic adhesives, cements, and restoratives are currently available. Compositions including fluoroaluminosilicate glass fillers (also known as glass ionomer or "GI" compositions) are among the most widely used types of dental materials. These compositions have a broad range of applications such as filling and restoration of carious lesions; cementing of, for example, a crown, an inlay, a bridge, or an orthodontic band; lining of cavity; core construction; and pit and fissure sealing.

There are currently two major classes of glass ionomers. The first class, known as conventional glass ionomers, generally contains as main ingredients a homopolymer or copolymer of an $\alpha,\beta$-unsaturated carboxylic acid, a fluoroaluminosilicate ("FAS") glass, water, and optionally a chelating agent such as tartaric acid. These conventional glass ionomers typically are supplied in powder/liquid formulations that are mixed just before use. The mixture undergoes self-hardening in the dark due to an ionic acid-base reaction between the acidic repeating units of the polycarboxylic acid and cations leached from the basic glass.

The second major class of glass ionomers is known as hybrid glass ionomer or resin-modified glass ionomers ("RMGI"). Like a conventional glass ionomer, an RMGI employs an FAS glass. An RMGI also contains a homopolymer or copolymer of an $\alpha,\beta$-unsaturated carboxylic acid, an FAS glass, and water; however, the organic portion of an RMGI is different. In one type of RMGI, the polyacid is modified to replace or end-cap some of the acidic repeating units with pendent curable groups and a photoinitiator is added to provide a second cure mechanism. Acrylate or methacrylate groups are typically employed as the pendant curable group. In another type of RMGI, the composition includes a polycarboxylic acid, an acrylate or methacrylate-functional monomer or polymer, and a photoinitiator. The polyacid may optionally be modified to replace or end-cap some of the acidic repeating units with pendent curable groups. A redox or other chemical cure system may be used instead of or in addition to a photoinitiator system. RMGI compositions are usually formulated as powder/liquid or paste/paste systems, and contain water as mixed and applied. They may partially or fully harden in the dark due to the ionic reaction between the acidic repeating units of the polycarboxylic acid and cations leached from the glass, and commercial RMGI products typically also cure on exposure of the cement to light from a dental curing lamp.

There are many important benefits provided by glass ionomer compositions. For example, fluoride release from glass ionomers tends to be higher than from other classes of dental compositions such as metal oxide cements, compomer cements, or fluoridated composites, and thus glass ionomers are believed to provide enhanced cariostatic protection. Another advantage of glass ionomer materials is the very good clinical adhesion of such cements to tooth structure, thus providing highly retentive restorations. Since conventional glass ionomers do not need an external curing initiation mode, they can generally be placed in bulk as a filling material in deep restorations, without requiring layering.

One of the drawbacks of conventional glass ionomers is that these compositions are somewhat technique sensitive when mixed by hand. They are typically prepared from a powder component and a liquid component, thus requiring weighing and mixing operations prior to application. The accuracy of such operations depends in part on operator skill and competency. When mixed by hand, the powder component and the liquid component are usually mixed on paper with a spatula. The mixing operation must be carried out within a short period of time, and a skilled technique is needed in order for the material to fully exhibit the desired characteristics (i.e., the performance of the cement can depend on the mixture ratio and the manner and thoroughness of mixing). Alternatively, some of these inconveniences and technique sensitivities have been improved by utilization of powder liquid capsule dispensing systems that contain the proper proportion of the powder and liquid components. While capsules provide proper proportions of the powder and liquid components, they still require a capsule activation step to combine the two components followed by mechanical mixing in a dental triturator.

Conventional glass ionomers may also be quite brittle as evidenced by their relatively low flexural strength. Thus restorations made from conventional glass ionomers tend to be more prone to fracture in load bearing indications. In addition, glass ionomers are often characterized by high visual opacity (i.e., cloudiness), especially when they come into contact with water at the initial stage of hardening, resulting in relatively poor aesthetics.

Cured RMGIs typically have increased strength properties (e.g., flexural strength), are less prone to mechanical fracture than conventional glass ionomers, and typically require a primer or conditioner for adequate tooth adhesion.

SUMMARY

One of the most significant disadvantages in using a conventional glass ionomer material is the lack of aesthetics, due to a high mismatch in refractive index between the acid-reactive glass filler and the glass ionomer matrix. This mismatch in refractive index leads to scattering of light at the interface between the different phases. By utilizing a filler comprised of nanoparticles, such as a metal oxide nanofiller, dispersed in the water/polyacid solution, the refractive index of the liquid phase can be increased. This leads to a better match of the refractive index of the matrix to the refractive index of the acid-reactive filler, leading to a much more optically transparent or translucent material. This in turn leads to the ability to provide an index matched, or aesthetic glass ionomer material.

The present invention provides stable ionomer compositions containing nanofillers that provide the compositions with enhanced optical translucency. In one embodiment, the present invention features a hardenable dental composition comprising a polyacid, an acid-reactive filler, a nanofiller; an optional polymerizable component; and water. The combined mixture of the polyacid, nanofiller, water and optional polymerizable component is generally within 4 percent of the refractive index of the acid-reactive filler, typically within 3 percent thereof, more typically within 1 percent thereof, and even more typically within 0.5 percent thereof. The refractive index of the combined mixture may be measured in the hardened state or the unhardened state.

Generally, the polymerizable component is an ethylenically unsaturated compound, optionally with acid functionality. The polyacid component of the composition typically comprises a polymer having a plurality of acidic repeating groups. The polymer may be substantially free of polymerizable groups, or alternatively it may comprise a plurality of polymerizable groups.

In one embodiment, the acid-reactive filler is selected from metal oxides, glasses, metal salts, and combinations thereof. Typically, the acid-reactive filler comprises an FAS glass. In some embodiments, the nanofiller may have a refractive index higher than the refractive index of the acide-reactive filler.

In another embodiment of the invention, the acid-reactive filler comprises an oxyfluoride material, which is typically nanostructured, e.g., provided in the form of nanoparticles. Generally, the acid-reactive oxyfluoride material is non-fused and includes at least one trivalent metal (e.g., aluminum, lanthanum, etc.), oxygen, fluorine, and at least one alkaline earth metal (e.g. strontium, calcium, barium, etc.). The oxyfluoride material may be in the form of a coating on particles or nanoparticles, such as metal oxide particles (e.g., silica).

The compositions of the invention may also include one or more optional additives, such as, for example, other fillers, pyrogenic fillers, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, medicaments, indicators, dyes, pigments, wetting agents, tartaric acid, chelating agents, surfactants, buffering agents, viscosity modifiers, thixotropes, polyols, antimicrobial agents, anti-inflammatory agents, antifungal agents, stabilizers, agents for treating xerostomia, desensitizers, and combinations thereof.

The compositions of the invention may further include a photoinitiator system and/or a redox cure system.

In some embodiments, the nanofiller comprises a nanocluster that contains reactive ions.

Additionally, the compositions may be provided in the form of a multi-part system in which the various components are divided into two or more separate parts. Typically, the composition is a two-part system, such as a paste-paste composition, a paste-liquid composition, a paste-powder composition, or a powder-liquid composition.

One of the features of the present invention is that it provides an optically translucent ionomer composition while potentially utilizing a reduced amount of acid-reactive filler than conventional glass ionomers. Typically, the compositions of the invention comprise less than 85 percent by weight acid-reactive filler when the two part compositions comprise a powder and liquid. Compositions comprising less than 75% and more typically less than 50% acid-reactive filler may be preferable for the preparation of a two-part, paste-paste composition, which is generally desirable because of the ease of mixing and dispensing of such a system compared to, for example, a powder-liquid system.

Compositions according to the invention are useful in a variety of dental and orthodontic applications, including dental restoratives, dental adhesives, dental cements, cavity liners, orthodontic adhesives, dental sealants, and dental coatings. The compositions may be used to prepare a dental article by hardening to form, for example, dental mill blanks, dental crowns, dental fillings, dental prostheses, and orthodontic devices.

The ionomer compositions of the invention generally exhibit good aesthetics, low visual opacity (generally no more than about 0.50 upon hardening, as determined by the Visual Opacity (MacBeth Values) Test Method described herein), radiopacity, durability, improved polish, polish retention, good wear properties, good physical properties including mechanical strengths, e.g., flexural, diametral, tensile and compressive strengths, and good adhesive strength to tooth structures. Furthermore, the compositions may also provide adhesion to both dentin and enamel without the need for primers, etchants, or preconditioners.

Other features and advantages of the present invention will be apparent from the following detailed description thereof, and from the claims.

Definitions

By "hardenable" is meant that the composition can be cured or solidified, e.g. by heating, chemical cross-linking, radiation-induced polymerization or crosslinking, or the like.

By "filler" is meant a particulate material suitable for use in the oral environment. Dental fillers generally have an average particle size of at most 100 micrometers.

By "nanofiller" is meant a filler having an average primary particle size of at most 100 nanometers. The nanofiller component may be a single nanofiller or a combination of nanofillers. Typically the nanofiller comprises non-pyrogenic nanoparticles or nanoclusters.

By "paste" is meant a soft, viscous mass of solids dispersed in a liquid.

By "acid-reactive filler" is meant a filler that chemically reacts in the presence of an acidic component.

By "oxyfluoride" is meant a material in which atoms of oxygen and fluorine are bonded to the same atom (e.g., aluminum in an aluminum oxyfluoride). Generally, at least 50% of the fluorine atoms are bonded to an atom bearing an oxygen atom in an oxyfluoride material.

By "nanostructured" is meant a material in a form having at least one dimension that is, on average, at most 100 nanometers (e.g., nanosized particles). Thus, nanostructured materials refer to materials including, for example, nanoparticles as defined herein below; aggregates of nanoparticles; materials coated on particles, wherein the coatings have an average thickness of at most 100 nanometers; materials coated on aggregates of particles, wherein the coatings have an average thickness of at most 100 nanometers; materials infiltrated in porous structures having an average pore size of at most 100 nanometers; and combinations thereof. Porous structures include, for example, porous particles, porous aggregates of particles, porous coatings, and combinations thereof.

As used herein "nanoparticles" is used synonymously with "nanosized particles," and refers to particles having an average size of at most 100 nanometers. As used herein for a spherical particle, "size" refers to the diameter of the particle. As used herein for a non-spherical particle, "size" refers to the longest dimension of the particle.

By "nanocluster" is meant an association of nanoparticles drawn together by relatively weak intermolecular forces that cause them to clump together, i.e. to aggregate. Typically, nanoclusters have an average size of at most 10 micrometers.

The term "ethylenically unsaturated compounds with acid functionality" is meant to include monomers, oligomers, and polymers having ethylenic unsaturation and acid and/or acid-precursor functionality. Acid-precursor functionalities include, for example, anhydrides, acid halides, and pyrophosphates.

By "dental compositions and dental articles" is meant to include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like).

DETAILED DESCRIPTION

The present invention provides ionomer compositions and methods for making aesthetic ionomer materials for use in dental restorations. The ionomer compositions typically include a liquid phase that includes a polyacid and a solid phase that includes an acid-reactive filler. This invention utilizes selected nanofillers comprised of certain nanoparticles, typically metal oxide nanoparticles, to increase the refractive index of the liquid phase into which the nanofiller is dispersed and stabilized. This, in turn, allows a match in refractive index of the liquid phase of the ionomer material, which is traditionally aqueous, with the acid-reactive filler leading to a much more optically transparent or translucent material. The liquid phase typically comprises water, a polyacid, an optional polymerizable component, optional additional additives (tartaric acid, for example, for reaction rate adjustment), and a nanofiller that has a refractive index higher than that of the liquid phase without nanofiller. This liquid phase is then mixed with an acid-reactive filler and allowed to react over a set time period to form a hardened ionomer material. By including a nanofiller in the composition such that the refractive index of a combined mixture of the polyacid, nanofiller, water and optional polymerizable component is within about 3–4 percent of the acid reactive filler, the composition is provided with improved properties including enhanced aesthetics (e.g., low visual opacity, high optical translucency) as compared to previously known ionomer compositions.

The refractive index of the combined mixture of the polyacid, the nanofiller, the water, and the optional polymerizable component can be measured in the unhardened state or the hardened state. The refractive index of the mixture in the unhardened state may be the same as it is in the hardened state, but it also may be different. If the refractive index changes after hardening, typically the refractive index after hardening would be matched to the refractive index of the acid-reactive filler. An objective of matching the refractive indices is to obtain the best visual opacity (best clarity) of the hardened composition. The hardening of the combined mixture can be accomplished by techniques known to one skilled in the art, e.g., by adding an acid-reactive filler as a separate, undispersed phase; light-curing if a photopolymerizable component is present; adding a redox system if a free-radically polymerizable component is present.

Polymerizable Component

As mentioned above, the hardenable dental compositions of the present invention optionally include a polymerizable component. The polymerizable component can optionally be an ethylenically unsaturated compound with or without acid functionality.

The polymerizable component of the present invention can be part of a hardenable resin. These resins are generally thermosetting materials capable of being hardened to form a polymer network including, for example, acrylate-functional materials, methacrylate-functional materials, epoxy-functional materials, vinyl-functional materials, and mixtures thereof. Typically, the hardenable resin is made from one or more matrix-forming oligomer, monomer, polymer, or blend thereof.

In certain embodiments where the dental composition disclosed in the present application is a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies, and mixtures and derivatives thereof.

One class of preferred hardenable materials includes materials having polymerizable components with free radically active functional groups. Examples of such materials include monomers having one or more ethylenically unsaturated groups, oligomers having one or more ethylenically unsaturated groups, polymers having one or more ethylenically unsaturated groups, and combinations thereof.

In the class of hardenable resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200–500); copolymerizable mixtures of acrylated monomers such as those in U.S. Pat. No. 4,652, 274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0 373 384 (Wagenknecht et al.), EP-0 201 031 (Reiners et al.), and EP-0 201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

Polymerizable Component with Acid Functionality

When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

Such compounds include, for example, α,β-unsaturated acidic compounds such as glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid, and the like, may be used as components in the hardenable resin system.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Ser. No. 10/729,497; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

When ethylenically unsaturated compounds with acid functionality are present, the compositions of the present invention typically include at least 1% by weight, more typically at least 3% by weight, and most typically at least 5% by weight ethylenically unsaturated compounds with acid functionality, based on the total weight of the unfilled composition. Typically, compositions of the present invention include at most 50% by weight, more typically at most 40% by weight, and most typically at most 30% by weight ethylenically unsaturated compounds with acid functionality, based on the total weight of the unfilled composition.

Partial or complete hardening of the composition may occur through an acid-reactive filler/polyacid reaction (i.e. an acid/base reaction). In certain embodiments, the composition also contains a photoinitiator system that upon irradiation with actinic radiation initiates the polymerization (or hardening) of the composition. Such photopolymerizable compositions can be free radically polymerizable.

Free Radical Initiation Systems

For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

Suitable photoinitiators (i.e., photoinitiator systems that include one or more compounds) for polymerizing free radically photopolymerizable compositions include binary and ternary systems. Typical ternary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl) borate. Preferred photosensitizers are monoketones and diketones that absorb some light within a range of about 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione, and other 1-aryl-2-alkyl-1,2 ethanediones, and cyclic alpha diketones. Most preferred is camphorquinone. Preferred electron donor compounds include substituted amines, e.g., ethyl dimethylaminobenzoate. Other suitable ternary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include, for example, bis(2,4,6-trimethylbenzoyl)phenyl phosphine oxide available under the trade designation IRGACURE 819 from Ciba Specialty Chemicals, Tarrytown, N.Y.; bis(2,6-dimethoxybenzoyl)-(2,4,4-trimethylpentyl) phosphine oxide available under the trade designation CGI 403 from Ciba Specialty Chemicals; a 25:75 mixture, by weight, of bis(2,6-dimethoxybenzoyl)-2,4,4-trimethylpentyl phosphine oxide and 2-hydroxy-2-methyl-1-phenylpropan-1-one available under the trade designation IRGACURE 1700 from Ciba Specialty Chemicals; a 1:1 mixture, by weight, of bis(2,4,6-trimethylbenzoyl)phenyl phosphine oxide and 2-hydroxy-2-methyl-1-phenylpropane-1-one available under the trade designation DAROCUR 4265 from Ciba Specialty Chemicals; and ethyl 2,4,6-trimethylbenzylphenyl phosphinate available under the trade designation LUCIRIN LR8893X from BASF Corp., Charlotte, N.C.

Typically, the phosphine oxide initiator is present in the photopolymerizable composition in catalytically effective amounts, such as from 0.1% by weight to 5% by weight, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1% by weight to 5% by weight, based on the total weight of the composition. Useful amounts of other initiators are well known to those of skill in the art.

Another free-radical initiator system that can alternatively be used in the dental materials of the invention includes the class of ionic dye-counterion complex initiators including a borate anion and a complementary cationic dye. Borate salt photoinitiators are described, for example, in U. S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.).

The hardenable resins of the present invention can include redox cure systems that include a polymerizable component (e.g., an ethylenically unsaturated polymerizable component) and redox agents that include an oxidizing agent and a reducing agent. Suitable polymerizable components and redox agents that are useful in the present invention are described in U.S. Pat. Publication No. 2003/0166740 (Mitra et al.) and U.S. Pat. Publication No. 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include, for example, ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and combinations thereof. Preferably, the reducing agent is an amine.

Suitable oxidizing agents will also be familiar to those skilled in the art, and include, for example, persulfuric acid and salts thereof, such as sodium, potassium, ammonium, cesium, and alkyl ammonium salts. Additional oxidizing agents include, for example, peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and combinations thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the hardenable composition as described, for example, in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the hardenable composition except for the filler, and observing whether or not a hardened mass is obtained.

Preferably, the reducing agent is present in an amount of at least 0.01% by weight, and more preferably at least 0.10% by weight, based on the total weight (including water) of the components of the hardenable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described, for example, in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. and at most 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Photoinitiator compounds are preferably provided in dental compositions disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile.

Polyacid

Compositions of the present invention include at least one polyacid, which may be a non-curable or non-polymerizable polyacid, or a curable or polymerizable polyacid (e.g., a resin-modified polyacid). Typically, the polyacid is a polymer having a plurality of acidic repeating units and a plurality of polymerizable groups. In alternative embodiments, the polyacid may be substantially free of polymerizable groups. The polyacid needs not be entirely water soluble, but it should be at least sufficiently water-miscible so that it does not undergo substantial sedimentation when combined with other aqueous components. Suitable polyacids are listed in U.S. Pat. No. 4,209,434 (Wilson et al.), column 2, line 62, to column 3, line 6. The polyacid should have a molecular weight sufficient to provide good storage, handling, and mixing properties. A typical weight average molecular weight is 5,000 to 100,000, evaluated against a polystyrene standard using gel permeation chromatography.

In one embodiment, the polyacid is a curable or polymerizable resin. That is, it contains at least one ethylenically unsaturated group. Suitable ethylenically unsaturated polyacids are described in U.S. Pat. No. 4,872,936 (Engelbrecht), e.g., at columns 3 and 4, and EP 323 120 B1 (Mitra), e.g., at page 3, line 55 to page 5, line 8. Typically, the numbers of acidic groups and ethylenically unsaturated groups are adjusted to provide an appropriate balance of properties in the dental composition. Polyacids in which 10% to 70% of the acidic groups have been replaced with ethylenically unsaturated groups are preferred.

In other embodiments, the polyacid is hardenable in the presence of, for example, an acid-reactive filler and water, but does not contain ethylenically unsaturated groups. That is, it is an oligomer or polymer of an unsaturated acid. Typically, the unsaturated acid is an oxyacid (i.e., an oxygen containing acid) of carbon, sulfur, phosphorous, or boron. More typically, it is an oxyacid of carbon. Such polyacids include, for example, polyalkenoic acids such as homopolymers and copolymers of unsaturated mono-, di-, or tricarboxylic acids. Polyalkenoic acids can be prepared by the homopolymerization and copolymerization of unsaturated aliphatic carboxylic acids, e.g., acrylic acid, 2-choloracrylic acid, 3-choloracrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include, for example, unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be substantially free of unpolymerized monomers.

The amount of polyacid should be sufficient to react with the acid-reactive filler and to provide an ionomer composition with desirable hardening properties. Typically, the polyacid represents at least 1 wt-%, more typically at least 3 wt-%, and most typically at least 5 wt-%, based on the total weight of the unfilled composition. Typically, the polyacid represents at most 90 wt-%, more typically at most 60 wt-%, and most typically at most 30 wt-%, based on the total weight of the unfilled composition.

Acid-Reactive Fillers

Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In another embodiment, the acid-reactive filler comprises a non-fused oxyfluoride material. The oxyfluoride material may include a trivalent metal, oxygen, fluorine, and an alkaline earth metal. Preferably the trivalent metal is aluminum, lanthanum, or combinations thereof. More preferably the trivalent metal is aluminum. Preferably the alkaline earth metal is strontium, calcium, barium, or combinations thereof. In some embodiments of the present invention, the oxyfluoride material may further include silicon and/or heavy metal (e.g., zirconium, lanthanum, niobium, yttrium, or tantalum), or more specifically, oxides, fluorides and/or oxyfluorides thereof.

In some embodiments of the present invention, at least a portion of the oxyfluoride material is nanostructured. Such nanostructured materials include the oxyfluoride material in the form of, for example, nanoparticles, coatings on particles, coatings on aggregates of particles, infiltrate in a porous structure, and combinations thereof. Preferably at least 90% by weight, more preferably at least 95% by weight, and most preferably at least 98% by weight of the oxyfluoride material is nanostructured.

A description of suitable oxyfluoride materials and their use in dental compositions is provided in a U.S. patent application entitled, "Acid Reactive Dental Fillers, Compositions, and Methods," Ser. No. 10/847805 filed on May 17, 2004.

The amount of acid-reactive filler should be sufficient to provide an ionomer composition having desirable mixing and handling properties before hardening and good physical and optical properties after hardening. Generally, the reactive filler represents less than about 85% of the total weight of the composition. Typically, the acid-reactive filler represents at least 10 wt-%, and more typically at least 20 wt-%, based on the total weight of the composition. Typically, the acid-reactive filler represents at most 75 wt-%, and more typically at most 50 wt-%, based on the total weight of the composition.

Nanofillers

The ionomer compositions of the invention are formulated with one or more nanofillers that impart the compositions with desirable aesthetic properties (e.g., high optical translucency). Suitable nanofillers may be either acid reactive or non-acid reactive and may include, but are not limited to silica; zirconia; oxides of titanium, aluminum, cerium, tin, yttrium, strontium, barium, lanthanum, zinc, ytterbium, bismuth, iron, and antimony; and combinations thereof. More typical nanofillers may include zirconia ($ZrO_2$); oxides of titanium (e.g., $TiO_2$), and ytterbium (e.g., $Y_2O_3$); and other metal oxides with high refractive indices. As used herein, "high refractive index" means a refractive index of typically at least 1.5, and more typically of at least 2.0. Titania dioxide and zirconia are particularly useful nanofillers, as they have very high refractive indices, and will require less weight of material than a lower refractive index material to match the refractive indices appropriately.

The nanofiller is selected so that the refractive index of a combined mixture of the polyacid, the nanofiller, the water, and the optional polymerizable component is generally within 4 percent of the refractive index of the acid-reactive filler, typically within 3 percent thereof, more typically within 1 percent thereof, and even more typically within 0.5 percent thereof.

The nanofillers typically have an average particle size of at most 100 nanometers and more typically at most 50 nanometers. Such nanofillers typically have an average particle size of at least 2 nanometers, more typically at least 5 nanometers, and even more typically at least 10 nanometers. In some embodiments, the nanofiller is in the form of nanoclusters, typically at least 80 percent by weight nanoclusters. In other embodiments, the nanofiller is in the form of a combination of nanoparticles and nanoclusters. Often a portion of the surface of the nanofiller is silane treated or otherwise chemically treated to provide one or more desired physical properties. Suitable nanofillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof.

Typically, the nanofillers of the present invention are non-pyrogenic fillers, however pyrogenic fillers can be added as optional additives to the dental compositions.

The acid-reactive, non-fused oxyfluoride materials described above that are at least partially nanostructured can be used as nanofillers in the present invention.

The amount of nanofiller should be sufficient to provide an ionomer composition having desirable mixing and handling properties before hardening and good physical and optical properties after hardening. Typically, the nanofiller represents at least 0.1 wt-%, more typically at least 5 wt-% or 10 wt-%, and most typically at least 20 wt-% based on the total weight of the composition. Typically, the nanofiller represents at most 80 wt-%, more typically at most 70 wt-%, and most typically at most 60 wt-%, based on the total weight of the composition.

Other Fillers

In addition to the acid-reactive filler and the nanofiller components, the compositions of the present invention can also optionally include one or more other fillers. Such fillers may be selected from one or more of a wide variety of materials suitable for the use in dental and/or orthodontic compositions.

The other filler can be an inorganic material. It can also be a crosslinked organic material that is insoluble in the resin component of the composition, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and silica particles (e.g., submicron pyrogenic silicas such as those available under the trade designations AEROSIL, including "OX 50," "130," "150" and "200" silicas from Degussa AG, Hanau, Germany and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Examples of useful silane coupling agents are those available from Crompton Corporation, Naugatuck, Conn., as SILQUEST A-174 and SILQUEST A-1230. For some embodiments of the present invention that include other fillers (e.g., dental restorative compositions), the compositions may include at least 1% by weight, more preferably at least 2% by weight, and most preferably at least 5% by weight other filler, based on the total weight of the composition. For such embodiments, compositions of the present invention preferably include at most 40% by weight, more preferably at most 20% by weight, and most preferably at most 15% by weight other filler, based on the total weight of the composition.

Water

The compositions of the invention contain water. The water can be distilled, deionized, or plain tap water. Typically, deionized water is used.

The amount of water should be sufficient to provide adequate handling and mixing properties and to permit the transport of ions, particularly in the filler-acid reaction. Preferably, water represents at least 2 wt-%, and more preferably at least 5 wt-%, of the total weight of ingredients used to form the composition. Preferably, water represents no greater than 90 wt-%, and more preferably no greater than 80 wt-%, of the total weight of ingredients used to form the composition.

Optional Additives

Optionally, the hardenable compositions may contain other solvents, cosolvents (e.g., alcohols) or diluents. If desired, the hardenable composition of the invention can contain additives such as indicators, dyes, pigments, inhibitors, accelerators, viscosity modifiers, wetting agents, tartaric acid, chelating agents, surfactants, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of the Compositions

The hardenable dental compositions of the present invention can be prepared by combining all the various components using conventional mixing techniques. As discussed above, the compositions may be partially or fully hardened by an ionic reaction between an acid-reactive filler and a polyacid. Optionally, the compositions may contain a polymerizable component and a photoinitiator and be hardened by photoinitiation, or may be partially or fully hardened by chemical polymerization such as a redox cure system in which the composition contains a free-radical initiator system, e.g., including an oxidizing agent and a reducing agent. Alternatively, the hardenable composition may contain different initiator systems, such that the composition can be both a photopolymerizable and a chemically polymerizable composition, as well as an ionically hardenable composition. The system of matching the refractive index may also be used in the formulation of dental compositions such as those described in U.S. patent application entitled, "Dental Compositions Containing Nanofillers and Related Methods," Ser. No. 10/847781 and U.S. patent application entitled, "Dental Compositions Containing Nanozirconia Fillers," Ser. No. 10/847782 both of which were filed on May 17, 2004.

The hardenable compositions of the invention can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, the polyacid, acid-reactive filler and water generally would not all be present in the same part, although any two of these may be grouped together in the same part along with any combination of other components. Furthermore, in a redox multi-part system, one part typically contains the oxidizing agent and another part typically contains the reducing agent. However, the reducing agent and oxidizing agent could be combined in the same part of the system if the components are kept separated, for example, through use of microencapsulation.

In some embodiments, two-part dental compositions of the present invention can be provided in a dual barrel syringe having a first barrel and a second barrel, wherein the part A resides in the first barrel and the part B resides in the second barrel. In other embodiments, two-part dental compositions of the present invention can be provided in a unit-dose capsule. In some embodiments, each part of a multi-part dental system can be mixed together using a static mixer.

The components of the hardenable composition can be included in a kit, where the contents of the composition are packaged to allow for storage of the components until they are needed.

When used as a dental composition, the components of the hardenable compositions can be mixed and clinically applied using conventional techniques. A curing light is generally required for the initiation of photopolymerizable compositions. The compositions can be in the form of composites or restoratives that adhere very well to dentin and/or enamel. Optionally, a primer layer can be used on the tooth tissue on which the hardenable composition is used. The compositions, e.g., containing a FAS glass or other fluoride-releasing material, can also provide very good long-term fluoride release. Some embodiments of the invention may provide glass ionomer cements or adhesives that can be cured in bulk without the application of light or other external curing energy, do not require a pre-treatment, have improved physical properties including improved flexural strength, and have high fluoride release for cariostatic effect.

The hardenable dental compositions of the invention are particularly well adapted for use in the form of a wide variety of dental materials. They can be used in prosthodontic cements, which are typically filled compositions (preferably containing greater than about 25 wt-% filler and up to about 60 wt-% filler). They can also be used in restoratives, which include composites which are typically filled compositions (preferably containing greater than about 50 wt-% filler and up to about 85 wt-% filler) that are hardened or polymerized after being disposed adjacent to a tooth, such as filling materials. They can also be used in prostheses that are shaped and hardened for final use (e.g., as a crown, bridge, veneer, inlay, onlay, or the like), before being disposed adjacent to a tooth. Such preformed articles can be ground or otherwise formed into a custom-fitted shape by the dentist or other user. Although the hardenable dental composition can be any of a wide variety of materials preferably, the composition is not a surface pre-treatment material (e.g., etchant, primer, bonding agent). Rather, preferably, the hardenable dental composition is a restorative (e.g., composite, filling material or prosthesis), cement, sealant, coating, or orthodontic adhesive.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Average Particle Size by TEM (Transmission Electron Microscopy) Test Method

Samples approximately 80-nm thick were placed on 200-mesh copper grids with carbon stabilized FORMVAR substrates (SPI Supplies, a division of Structure Probe, Inc., West Chester, Pa.). A transmission electron micrograph (TEM) was taken using a JEOL 200CX Instrument (JEOL, Ltd. of Akishima, Japan and sold by JEOL USA, Inc.) at 200 Kv. A population size of about 50–100 particles was measured and an average particle size was determined.

Refractive Index (RI) Test Method A

The refractive index values of liquid compositions were measured at room temperature utilizing a Abbe-3L Refractometer manufactured by Bausch and Lomb. Measurements were run in accord with manufacturer's recommendations and good laboratory practices.

Refractive Index (RI) Test Method B

The refractive index values of solid materials (e.g. glass fillers) were measured at room temperature by dispersing a solid test sample into optical liquids with different known specific refractive indexes. A kit with calibrated optical liquids is available from Cargille Laboratories (Cedar Grove, N.J.). Observations of the dispersions were made with a light microscope. The refractive index of the solid material was determined by using the Becke's line as a band of light that appears along the outer edge of the dispersed particles under microscopic investigation. The Becke's line indicates the relative difference or the equality between the refractive indices of the solid material and the optical liquid.

Visual Opacity (MacBeth Values) Test Method

Disc-shaped (1-mm thick×20-mm diameter) test samples were prepared by allowing mixed test samples to react and harden for 1 hour at 37° C. in a sealed container with water at the bottom but not in contact with the samples. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Opacity (HunterLab Values) Test Method

Disc-shaped (1.5-mm thick×15-mm diameter) test samples were prepared by allowing mixed test samples to react and harden at 36° C. and at least 95% relative humidity for 1 hour. Hardened samples were measured for opacity by using reflectometry and employing a HunterLab Color Measurement System (Labscan-2 0/45 SN-14014; HunterLab, Reston, Va.). Opacity in this test is defined as the ratio of the reflectance of the sample backed by black to the reflectance of the sample backed by white. The first measurement was designated the 1-hour Opacity value. Subsequently, the samples were immediately transferred into a vial and stored under 36° C. water for an additional 23 hours, after which the opacities were measured as before (24-Hour Opacity). Lower HunterLab opacity values indicate lower visual opacity and greater translucency of a material.

Compressive Strength (CS) Test Method

Compressive strength was evaluated by allowing a mixed test sample to react and harden for 1 hour at 36° C. in a sealed container with water at the bottom but not in contact with the sample. The hardened disc-shaped sample (4-mm diameter×6-mm thickness) was stored at 36° C. in water for an additional 23 hours. Compressive strength then was determined according to ISO Standard 9917-1 (1991) using a Zwick universal tester (Zwick GmbH & Co. KG, Ulm, Germany) operated at a crosshead speed of 1 millimeter per minute (mm/min). Results were reported as the average of 6 replicates.

Flexural Strength (CS) Test Method

Flexural strength of a test sample was evaluated as described for the CS Test Method above, except that a rectangular-shaped sample (25-mm length×2-mm width×2-mm thickness) was used and Flexural strength was determined according to ISO Standard 9917-2 (1998) using a Zwick universal tester (Zwick GmbH & Co. KG, Ulm, Germany) operated at a crosshead speed of 1 millimeter per minute (mm/min). Results were reported as the average of 6 replicates.

Abbreviations, Descriptions, and Sources of Materials

| Abbreviation | Description and Source of Material |
| --- | --- |
| OPTILAKE 3 TS | A silica/zirconia-treated titania sol containing 10 weight % titania in a water/ammonia solution (Catalysts and Chemicals Industry Corp, Japan). The particle size of the treated titania was 7.53 nm (standard deviation of 1.85 nm), as determined according to the TEM Test Method described herein |
| TS A1230-A | Titania sol (about 10% by weight silane-treated nanotitania filler) prepared as described under Starting Material Preparations. |
| TS A1230-B | Titania sol (about 10% by weight silane-treated nanotitania filler) prepared as described under Starting Material Preparations. |
| SILQUEST A-1230 | PEG Silane used for silane treatment of fillers (Cromption Corporation, Naugatuck, CT) |
| FAS Filler A | Fluoroaluminasilica (FAS) glass filler available as KETAC Fil Plus Hand Mix; Particle size distribution with a d90-value of about 27 micrometers. (3M ESPE) (Refractive Index about 1.508 - determined according to the Refractive Index Test Method B described herein.) |
| FAS Filler B | Same as FAS Filler A, except further sieved and screened to obtain a particle size distribution with a d90-value of about 9 micrometers. |
| FAS Filler C | Schott Glass (Product No. G 018-117; average particle size 1.0 micrometers; Schott Electronic Packaging, GmbH, Landshut, Germany). The filler was silane-treated as described for Filler FAS VI in U.S. Pat. Publication No. 2003/0166740 (Mitra et al.). (Refractive Index about 1.515 - determined according to the Refractive Index Test Method B described herein.) |

-continued

| Abbreviation | Description and Source of Material |
|---|---|
| HEMA | 2-Hydroxyethyl methacrylate (Sigma-Aldrich, St. Louis, MO) |
| BisGMA | 2,2-Bis[4-(2-hydroxy-3-methacryloyloxy-propoxy)phenyl]propane; CAS No. 1565-94-2 |
| PEGDMA-400 | Polyethyleneglycol dimethacrylate (Sartomer 603; MW about 570; Sartomer, Exton, PA) |
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity ρ = 4.64. |
| IEM | 2-Isocyanatoethyl methacrylate (Sigma-Aldrich) |
| VBCP | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| GDMA | Glycerol dimethacrylate (Rhom and Tech, Inc., Darmstadt, Germany) |
| Kayamer PM-2 | Bis(methacryloxyethyl) phosphate (Nippon Kayaku, Japan) |
| Ebecryl 1830 | Polyester hexaacrylate resin (UCB-Radcure Specialties, Brussels, Belgium) |
| Zirconia Sol | Aqueous zirconia sol containing 16.95% zirconia, Buhler Z-W4, (Buhler Ltd, Uzwil, Switzerland). Average particle size of the zirconia was reported by the manufacturer to be 10 nm to 40 nm. |

Starting Materials Preparations

Polyacid A

Copolymer of Acrylic and Maleic Acids

An aqueous solution of acrylic acid and maleic acid sodium salt (1 to 1.2 mole ratio) with added hydrogen peroxide initiator (5-fold molar excess with respect to the acrylic acid) was heated at 90–100° C. over 5 hours. After cooling to room temperature, the solution was acidified with sulfuric acid to a pH of about 1. The resulting polyacid precipitate was purified by membrane filtration and isolated by spray drying to afford a powder that was characterized as poly(acrylic/maleic)acid having an average molecular weight (MW) of 10,000 to 12,000 g/mol.

Polyacid B

Copolymer of Acrylic and Maleic Acids

An aqueous solution of acrylic acid and maleic acid sodium salt (1 to 1.2 mole ratio) with added hydrogen peroxide initiator (0.1 molar ratio with respect to the acrylic acid) was heated at 90–100° C. over 5 hours. After cooling to room temperature, the solution was acidified with sulfuric acid to a pH of about 1. The resulting polyacid precipitate was purified by membrane filtration and isolated by spray drying to afford a powder that was characterized as poly(acrylic/maleic)acid having an average molecular weight (MW) of 28,000 to 32,000 g/mol.

Nanofiller A

Silane-Treated Nanotitania ("High-Level")

OPTILAKE 3 Titania Sol (200 g) was combined with SILQUEST A-1230 (12.026 g) and the resulting solution heated in a sealed container at 80° C. for 16 hours. The resulting solution was dried to a powder (designated Nanofiller A) that was found to disperse into water very effectively with slight heat and agitation (60–80° C. on a hotplate) to form an optically transparent solution.

Nanofiller B

Silane-Treated Nanotitania ("Low-Level")

OPTILAKE 3 Titania Sol (100 g) was combined with SILQUEST A-1230 (3 g) and the resulting solution heated in a sealed container at 80° C. for 16 hours. The resulting solution was dried to a powder (designated Nanofiller B) that was found to disperse into water very effectively with slight heat and agitation (60–80° C. on a hotplate) to form an optically transparent solution.

Nanofiller C

Silane-Treated Nanotitania ("Lower-Level")

OPTILAKE 3 Titania Sol (25 g) was combined with SILQUEST A-1230 (0.625 g) and the resulting solution heated in a sealed container at 80° C. for 16 hours. The resulting solution was dried to a powder (designated Nanofiller C) that was found to disperse into water very effectively with slight heat and agitation (60–80° C. on a hotplate) to form an optically transparent solution.

Titania Sol A1230-A (TS A1230-A)

Silane-Treated Nanotitania Sol ("High-Level")

OPTILAKE 3 Titania Sol (15 g) was combined with SILQUEST A-1230 (0.375 g) and the resulting solution heated in a sealed container at 80° C. for 16 hours and then cooled to room temperature. The resulting titania sol (about 10% by weight silane-treated nanotitania filler) was designated Titania Sol A1230-A (TS A1230-A).

Titania Sol A1230-B (TS A1230-B)

Silane-Treated Nanotitania Sol ("Low-Level")

OPTILAKE 3 Titania Sol (200 g) was combined with SILQUEST A-1230 (1.16 g) and the resulting solution heated in a sealed container at 80° C. for 16 hours and then cooled to room temperature. The resulting titania sol (about 10% by weight silane-treated nanotitania filler) was designated Titania Sol A1230-B (TS A1230-B).

Nanofiller D

Silane-Treated Nanozirconia

Zirconia Sol (100.0 g; 16.95 g zirconia) was charged into a 16-ounce glass jar followed by the addition with stirring of 1-methoxy-2-propanol (100 g; Sigma-Aldrich), SILQUEST A-174 (3.45 g) and SILQUEST A-1230 (2.4 g). The resulting mixture was stirred 10 minutes at room temperature, heated to 90° C. for 4.0 hours, and then the contents were concentrated via rotary evaporation to afford a liquid concentrate (59 g).

DI water (172 g) and concentrated ammonia/water (5.4 g; 29% NH3) were charged to a 500-ml beaker followed by the addition over about 5 minutes of the liquid concentrate to afford a white precipitate. The precipitate was recovered by vacuum filtration and washed with DI water. The resulting wet cake was dispersed in 1-methoxy-2-propanol (54 g) to afford a dispersion that contained 17.6% by weight silane-treated nanozirconia filler. The filler was designated as Nanofiller D.

The above dispersion (78.44 g) was combined with Resin A [HEMA (2.28 g) and PEGDMA-400 (3.73 g)] and the water and alcohol removed via rotary evaporation to afford a fluid dispersion that contained 70% by weight silane-treated nanozirconia filler. This was designated as Nanofiller D/Resin A.

Example 1

Aqueous Polyacid+Silane-Treated Nanotitania Filler

Nanofillers A and B were separately added at various levels to a 30% by weight aqueous solution of Polyacid A and the Refractive Index (RI) values of the resulting dispersions determined according to the RI Test Method A described herein. The various nanofiller levels and the measured RI values are provided in Table 1.

TABLE 1

| Run | Nanofiller A (%) | Nanofiller B (%) | Refractive Index (RI) |
|---|---|---|---|
| 1 | 0 | 0 | 1.3845 |
| 2 | 10 | 0 | 1.401 |
| 3 | 20 | 0 | 1.425 |
| 4 | 30 | 0 | 1.4425 |
| 5 | 40 | 0 | 1.4665 |
| 6 | 50 | 0 | 1.4975 |
| 7 | 0 | 30 | 1.4485 |
| 8 | 0 | 40 | 1.4778 |
| 9 | 0 | 50 | 1.5185 |

Examples 2–3 and Comparative Example 1

Aqueous Polyacid+Silane-Treated Nanotitania Filler+FAS Glass

A glass Ionomer (GI) composition was prepared by combining a 30% by weight aqueous solution of Polyacid A with 40% by weight Nanofiller A (Example 1/Run5; "liquid component") followed by the addition of FAS Filler A ("powder component"; RI approximately 1.508). The two components were thoroughly mixed in a 2:1 powder/liquid weight ratio to afford a paste that was designated Example 2 and that subsequently was allowed to harden for 1 hour at 37° C. in a sealed container with water at the bottom but not in contact with the sample.

A GI composition was prepared and hardened as described for Example 2, except that 50% Nanofiller A (Example 1/Run 6) was used. The resulting paste was designated Example 3 and subsequently allowed to harden.

A GI composition was prepared and hardened as described for Example 2, except that no nanofiller was used. The resulting paste was designated as Comparative Example 1 and subsequently allowed to harden.

The relative parts by weight of the components in the mixed powder/liquid compositions, are provided in Table 2A.

TABLE 2A

| Components (Parts by Weight) | Comp. Ex. 1 | Example 2 | Example 3 |
|---|---|---|---|
| FAS Filler A | 66.7 | 66.7 | 66.7 |
| Nanofiller A | 0 | 13.3 | 16.6 |
| Polyacid A | 10.0 | 6.0 | 5.0 |
| Water | 23.3 | 14.0 | 11.7 |
| Total | 100 | 100 | 100 |

The physical appearance and qualitative visual optical properties of hardened Examples 2 and 3 in comparison with the hardened Comparative Example 1 are provided in Table 2B.

TABLE 2B

| Example | Added Nanofiller | Appearance (Hardened Paste) | Optical Property* |
|---|---|---|---|
| Comparative Ex. 1 | None | Opaque | Unable to read lettering |
| 2 | 40% Nanofiller A | Opaque | Somewhat able to read lettering |
| 3 | 50% Nanofiller A | Translucent | Very able to read lettering |

*Optical property determined by ability to read lettering on a paper through a 2- to 3-mm thick sample of the hardened paste.

Examples 4–6

Aqueous Polyacid+Silane-Treated Nanotitania Filler+FAS Glass

A Glass Ionomer (GI) composition was prepared by combining a 30% by weight aqueous solution of Polyacid A with 40% by weight Nanofiller B ("liquid component"; Example 1/Run 8) followed by the addition of FAS Filler A ("powder component"). The two components were thoroughly mixed in a 2.5:1 powder/liquid weight ratio (i.e., 71.4% FAS Filler A loading) to afford a paste that was designated Example 4 and that subsequently was allowed to harden for 1 hour at 37° C. in a sealed container with water at the bottom but not in contact with the sample.

A GI composition was prepared and hardened as described for Example 4, except that 50% Nanofiller B (Example 1/Run 9) was used. The resulting paste was designated Example 5 and subsequently allowed to harden.

A GI composition was prepared and hardened as described for Example 4, except that a 50/50 mixture of 40% and 50% Nanofiller B was used. The resulting paste was designated Example 6 and subsequently allowed to harden.

A GI composition was prepared and hardened as described for Example 4, except that no nanofiller was used. The resulting paste was designated as Comparative Example 2 and subsequently allowed to harden.

The relative parts by weight of the components in the mixed powder/liquid compositions, are provided in Table 3A.

TABLE 3A

| Components (Parts by Weight) | Comp. Ex. 2 | Example 4 | Example 5 | Example 6 |
|---|---|---|---|---|
| FAS Filler A | 71.4 | 71.4 | 71.4 | 71.4 |
| Nanofiller B | 0 | 11.4 | 14.3 | 12.9 |
| Polyacid A | 8.6 | 5.2 | 4.3 | 4.7 |
| Water | 20.0 | 12.0 | 10.0 | 11.0 |
| Total | 100 | 100 | 100 | 100 |

The physical appearance, qualitative visual optical properties, and Visual Opacity (MacBeth Values determined according to the Visual Opacity Test Method A described herein) of hardened Examples 4–6 in comparison with the hardened Comparative Example 1 are provided in Table 3B.

TABLE 3B

| Example | Added Filler | Appearance (Hardened Paste) | Optical Property | Visual Opacity |
|---|---|---|---|---|
| Comp. Ex. 2 | None | Opaque | Unable to read lettering | 0.65 |
| 4 | 40% Nanofiller B | Translucent | Very able to read lettering | 0.49 |
| 5 | 50% Nanofiller B | Translucent | Very able to read lettering | NT* |
| 6 | 50—50 Mix of 40% & 50% Nanofiller B | Translucent | Very able to read lettering | 0.45 |

*NT—Not Tested

It can be concluded from the data in Tables 2B and 3B that the optical properties and Visual Opacity values of the GI compositions improved (i.e., became more translucent) as the RI of the FAS glass filler component was more closely matched by the RI of the water, polyacid, and nanofiller component.

Examples 7–9 and Comparative Examples 2–3

Glass Ionomer Compositions

Glass Ionomer (GI) compositions were prepared by mixing a Powder Part (containing polyacid and FAS glass filler components) with a Liquid Part (containing water and optional nanofiller components) and the resulting pastes (Examples 7–9 and Comparative Examples 2–3) allowed to harden for 1 hour at 36° C. and at least 95% relative humidity. The nanofiller component was introduced in the form of TS A1230-A (Titania Sol containing about 10% by weight silane-treated nanotitania or, alternatively, a more concentrated form (e.g. about 20% by weight) of the same sol). The relative parts by weight of the powder and liquid components, the parts by weight components in the mixed paste compositions, and the powder/liquid weight ratios utilized are provided in Table 4.

The hardened compositions were evaluated for Compressive Strength, Flexural Strength, and 1-Hour and 24-Hour Opacity (HunterLab Values) according to the Test Methods described herein and the results are reported in Table 4.

TABLE 4

| Parts | Components (Parts by Weight) | Comp. Ex. 2 | Ex. 7 | Ex. 8 | Comp. Ex. 3 | Ex. 9 |
|---|---|---|---|---|---|---|
| Powder Part | FAS Filler A | 88.0 | 88.0 | 88.0 | 0.0 | 0.0 |
| | FAS Filler B | 0.0 | 0.0 | 0.0 | 81.8 | 81.8 |
| | Polyacid B | 12.0 | 12.0 | 12.0 | 18.2 | 18.2 |
| Liquid Part | TS A1230-A* | 0.0 | 10.0 | 20.0 | 0.0 | 10.0 |
| | Water | 100.0 | 90.0 | 80.0 | 100.0 | 90.0 |
| | Powder/Liquid Ratio: | 7.2 | 7.2 | 7.2 | 6.6 | 6.6 |
| Mixed Paste | FAS Filler A | 77.3 | 77.3 | 77.3 | 0.0 | 0.0 |
| | FAS Filler B | 0.0 | 0.0 | 0.0 | 71.2 | 71.2 |
| | Polyacid B | 10.5 | 10.5 | 10.5 | 15.6 | 15.6 |
| | TS A1230-A* | 0.0 | 1.2 | 2.4 | 0.0 | 1.3 |
| | Water | 12.2 | 11.0 | 9.8 | 13.2 | 11.8 |
| | Total | 100 | 100 | 100 | 100 | 100 |
| Evaluation Results: | | | | | | |
| | Comp. Strength (MPa) | 117 | 175 | 214 | 258 | 266 |
| | Flex. Strength (MPa) | 24 | 37 | 38 | NT** | NT |
| | 1-Hour Opacity | 89.7 | 80.5 | 78.0 | 79.3 | 74.6 |
| | 24-Hour Opacity | 89.1 | 79.9 | 79.2 | 78.2 | 74.6 |

*Parts by weight indicated on dry weight basis; water content of the TS A1230-A included in the water component value.
**NT—Not Tested Examples 10–20 and Comparative Example 4

Glass Ionomer Compositions

Glass Ionomer (GI) compositions were prepared by mixing a Powder Part (containing polyacid and FAS glass filler components) with a Liquid Part (containing water and optional nanofiller components) and the resulting pastes (Examples 10–20 and Comparative Example 4) allowed to harden for 1 hour at 36° C. and at least 95% relative humidity. The nanofiller component was introduced in the form of TS A1230-B, OPTILAKE 3 TS, or Nanofiller C. The relative parts by weight of the powder and liquid components, the parts by weight components in the mixed paste compositions, and the powder/liquid weight ratios utilized are provided in Tables 5A and 5B.

The hardened compositions were evaluated for Compressive Strength, Flexural Strength, and 1-Hour and 24-Hour Opacity (HunterLab Values) according to the Test Methods described herein and the results are reported in Tables 5A and 5B.

TABLE 5A

| Parts | Components (Parts by Weight) | Comp. Ex. 4 | Ex. 10 | Ex. 11 | Ex. 12 | Ex. 13 | Ex. 14 |
|---|---|---|---|---|---|---|---|
| Powder Part | FAS Filler A | 88.0 | 88.0 | 88.0 | 88.0 | 88.0 | 88.0 |
| | Polyacid A | 12.0 | 12.0 | 12.0 | 12.0 | 12.0 | 12.0 |
| Liquid Part | TS A1230-B* | 0.0 | 1.7 | 3.3 | 6.3 | 7.7 | 9.1 |
| | Water | 100.0 | 98.3 | 96.8 | 93.7 | 92.3 | 90.9 |
| | Powder/Liquid Ratio: | 7.2 | 7.0 | 6.9 | 6.6 | 6.4 | 6.3 |
| Mixed | FAS Filler A | 77.3 | 77.0 | 76.8 | 76.4 | 76.2 | 75.9 |

TABLE 5A-continued

| Parts | Components (Parts by Weight) | Comp. Ex. 4 | Ex. 10 | Ex. 11 | Ex. 12 | Ex. 13 | Ex. 14 |
|---|---|---|---|---|---|---|---|
| Paste | Polyacid A | 10.5 | 10.5 | 10.5 | 10.4 | 10.4 | 10.4 |
| | TS A1230-B* | 0.0 | 0.2 | 0.4 | 0.8 | 1.0 | 1.3 |
| | Water | 12.2 | 12.2 | 12.3 | 12.4 | 12.4 | 12.5 |
| | Total | 100 | 100 | 100 | 100 | 100 | 100 |
| | Evaluation Results: | | | | | | |
| | Comp. Strength (MPa) | 112 | NT** | NT | NT | NT | NT |
| | Flex. Strength (MPa) | 15 | NT | NT | NT | NT | NT |
| | 1-Hour Opacity | 92.4 | 85.9 | 83.8 | 82.9 | 87.4 | 86.7 |
| | 24-Hour Opacity | 92.5 | 86.1 | 86.4 | 85.9 | 87.4 | 86.3 |

*Parts by weight indicated on dry weight basis; water content of the TS A1230-B included in the water component value.
**NT—Not Tested

TABLE 5B

| Parts | Components (Parts by Weight) | Ex. 15 | Ex. 16 | Ex. 17 | Ex. 18 | Ex. 19 | Ex. 20 |
|---|---|---|---|---|---|---|---|
| Powder Part | FAS Filler A | 88.0 | 88.0 | 88.0 | 88.0 | 88.0 | 88.0 |
| | Polyacid A | 12.0 | 12.0 | 12.0 | 12.0 | 12.0 | 12.0 |
| Liquid Part | TS A1230-B* | 10.0 | 0.0 | 0.0 | 10.0 | 0.0 | 0.0 |
| | OPTILAKE 3 TS* | 0.0 | 10.0 | 10.0 | 0.0 | 0.0 | 0.0 |
| | Nanofiller C | 0.0 | 0.0 | 0.0 | 0.0 | 20.0 | 40.0 |
| | Water | 90.0 | 90.0 | 90.0 | 90.0 | 80.0 | 60.0 |
| | Powder/Liquid Ratio: | 6.2 | 6.2 | 7.2 | 7.2 | 7.2 | 7.2 |
| Mixed Paste | FAS Filler A | 75.8 | 75.8 | 77.3 | 77.3 | 77.3 | 77.3 |
| | Polyacid A | 10.3 | 10.3 | 10.5 | 10.5 | 10.5 | 10.5 |
| | TS A1230-B* | 1.4 | 0.0 | 0.0 | 1.2 | 0.0 | 0.0 |
| | OPTILAKE 3 TS* | 0.0 | 1.4 | 1.2 | 0.0 | 0.0 | 0.0 |
| | Nanofiller C | 0.0 | 0.0 | 0.0 | 0.0 | 2.4 | 4.9 |
| | Water | 12.5 | 12.5 | 11.0 | 11.0 | 9.8 | 7.3 |
| | Total | 100 | 100 | 100 | 100 | 100 | 100 |
| | Evaluation Results: | | | | | | |
| | Comp. Strength (MPa) | 97 | 106 | 182 | 171 | 179 | 184 |
| | Flex. Strength (MPa) | 16 | 16 | 31 | 30 | 28 | 37 |
| | 1-Hour Opacity | 86.3 | 89.6 | 87.7 | 85.4 | 86.3 | 85.4 |
| | 24-Hour Opacity | 88.1 | 91.3 | 90.3 | 88.2 | 86.6 | 87.0 |

*Parts by weight indicated on dry weight basis; water content of the TS A1230-B and OPTILAKE 3 TS included in the water component value.

Example 21 and Comparative Example 5

Resin Modified Glass Ionomer Compositions

Two first paste compositions (designated as Pastes A1 and A2) were prepared by combining the ingredients (indicated as parts by weight) as listed in Table 6A. Filler D (silane-treated nanozirconia) was added to the compositions as part of a fluid dispersion comprised of 70% nanozirconia in Resin A (HEMA/PEGDMA-400—See Starting Material Preparation for Nanofiller D). One second paste composition (designated as Paste B) was prepared by combining the ingredients (indicated as parts by weight) as listed in Table 6B.

TABLE 6A

Paste A Compositions

| Components (Parts by Weight) | Paste A1 | Paste A2 |
|---|---|---|
| HEMA | 12.03 | 27.59 |
| PEGDMA-400 | 12.28 | 28.18 |
| Nanofiller D | 56.39 | 0 |
| DI Water | 19.28 | 44.23 |
| Total | 100 | 100 |

TABLE 6B

Paste B Composition

| Components (Parts by Weight) | Paste B |
|---|---|
| HEMA | 45.82 |
| VBCP | 24.67 |
| GDMA | 6.21 |
| BisGMA | 10.34 |
| Kayamer PM-2 | 11.70 |

TABLE 6B-continued

Paste B Composition

| Components (Parts by Weight) | Paste B |
|---|---|
| Ebecryl 1830 | 1.3 |
| Total | 100 |

Hardenable compositions (Example 21R and Comparative Example 5R—Resins Only) were prepared by spatulating each of the A pastes with Paste B for about 25 seconds on a mix pad. The Refractive Index (RI) values of these compositions were determined according to the RI Test Method A described herein. To portions of these compositions was added FAS Filler C to afford Example 21 and Comparative Example 5. The relative parts by weight of the components in the compositions are provided in Table 7.

The hardenable compositions were evaluated for Visual Opacity according to a modification of the Visual Opacity (MacBeth Values) Test Method described herein and the results are reported in Table 7. (In the modified Test Method, a mixed test sample (immediately after mixing and not light-cured) was placed between glass microscope slides using a 1-mm thick stainless steel washer as a mold. The visual opacity of the sample was then measured using the MacBeth densitometer.)

TABLE 7

Past A + Paste B Compositions

| Components (Parts by Weight) | Example 21R (Resin Only) Paste A1 + Paste B | Example 21 (with FAS Glass) Paste A1 + Paste B | Comp. Ex. 5R (Resin Only) Paste A2 + Paste B | Comp. Ex. 5 (with FAS Glass) Paste A2 + Paste B |
|---|---|---|---|---|
| HEMA | 25.45 | 12.45 | 39.10 | 19.55 |
| PEGDMA-400 | 6.77 | 3.8 | 10.4 | 5.2 |
| VBCP | 10.14 | 4.7 | 15.57 | 7.78 |
| GDMA | 2.55 | 1.18 | 3.92 | 1.96 |
| BisGMA | 4.25 | 1.97 | 6.53 | 3.26 |
| Kayamer PM-2 | 4.805 | 2.23 | 7.38 | 3.69 |
| Ebecryl 1830 | .533 | 0.25 | 0.82 | 0.41 |
| Nanofiller D | 34.89 | 17.44 | 0 | 0 |
| DI Water | 10.62 | 5.96 | 16.32 | 8.16 |
| FAS Filler C (RI = 1.515) | 0 | 50 | 0 | 50 |
| Total | 100 | 100 | 100 | 100 |
| Evaluation Results: | | | | |
| Refractive index | 1.5165 | | 1.4536 | |
| Visual Opacity (VO) | 0.2 (translucent) | 0.3 (translucent) | | 0.80 (opaque) |

It can be observed from Table 7 that the inclusion of Nanofiller D into the resin composition increased the Refractive Index of the resin from 1.4536 to 1.5165 (Compare Ex. 21 R with Comparative Ex. 5R), thus more closely matching the Refractive Index of the FAS Filler C (RI=1.515). The addition of the FAS Filler C to the resin composition without Nanofiller D provided a resin-modified glass composition (Comparative Ex. 5) with very poor optical properties (VO=0.80), whereas the addition of the FAS Filler C to the resin composition with Nanofiller D provided a resin-modified glass composition (Example 21) with excellent optical properties (VO=0.3).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hardenable dental composition comprising:
   (a) a polyacid;
   (b) an acid-reactive filler;
   (c) a nanofiller;
   (d) water; and
   (e) an optional polymerizable component;
wherein the refractive index of a combined mixture of the polyacid, the nanofiller, the water, and the optional polymerizable component is within 4 percent of the refractive index of the acid-reactive filler.

2. The composition of claim 1, wherein the refractive index of the combined mixture of the polyacid, the nanofiller, the water, and the optional polymerizable component is within 3 percent of the refractive index of the acid-reactive filler.

3. The composition of claim 1, wherein the refractive index of the combined mixture of the polyacid, the nanofiller, the water, and the optional polymerizable component is within 1 percent of the refractive index of the acid-reactive filler.

4. The composition of claim 1, comprising a polymerizable component.

5. The composition of claim 4, wherein the polymerizable component comprises an ethylenically unsaturated compound.

6. The composition of claim 4, wherein the polymerizable component comprises an ethylenically unsaturated compound with acid functionality.

7. The composition of claim 1, wherein the polyacid comprises a polymer having a plurality of acidic repeating groups but is substantially free of polymerizable groups.

8. The composition of claim 7 comprising a polymerizable component.

9. The composition of claim 1, wherein the polyacid comprises a polymer having a plurality of acidic repeating groups and a plurality of polymerizable groups.

10. The composition of claim 9 comprising a polymerizable component.

11. The composition of claim 1, wherein the acid-reactive filler is selected from the group consisting of metal oxides, glasses, metal salts, and combinations thereof.

12. The composition of claim 11, wherein the acid-reactive filler comprises a fluoroaluminosilicate (FAS) glass.

13. The composition of claim 12, wherein the composition comprises less than 50 weight percent FAS glass.

14. The composition of claim 11, wherein the acid-reactive filler comprises an oxyfluoride material.

15. The composition of claim 14, wherein at least 90% by weight of the oxyfluoride material is nanostructured.

16. The composition of claim 1, wherein the nanofiller is acid reactive.

17. The composition of claim 1, wherein the nanofiller is non-acid reactive.

18. The composition of claim 1, wherein the nanofiller has an average particle size of no more than about 50 nanometers.

19. The composition of claim 1, wherein the nanofiller is present in an amount greater than 0.1 weight percent.

20. The composition of claim 1, wherein the nanofiller is present in an amount greater than 5 weight percent.

21. The composition of claim 1, wherein the nanofiller is present in an amount greater than 10 weight percent.

22. The composition of claim 1, wherein the nanofiller is present in an amount greater than 20 weight percent.

23. The composition of claim 1, wherein the nanofiller comprises particles selected from the group consisting of silica; zirconia; oxides of titanium, aluminum, cerium, tin, yttrium, strontium, barium, lanthanum, zinc, ytterbium, bismuth, iron, and antimony; and combinations thereof.

24. The composition of claim 1, wherein the nanofiller comprises a nanocluster.

25. The composition of claim 24, wherein the nanocluster contains reactive ions.

26. The composition of claim 1, wherein the nanofiller has a refractive index higher than the refractive index of the acid-reactive filler.

27. The composition of claim 1, wherein the nanofiller has a refractive index higher than 1.5.

28. The composition of claim 1, wherein the nanofiller has a refractive index higher than 2.0.

29. The composition of claim 1, wherein the nanofiller comprises an oxide of titanium having a chemically-treated surface.

30. The composition of claim 29, wherein the nanofiller comprises titanium dioxide having a silane-treated surface.

31. The composition of claim 1, wherein the composition upon hardening has a visual opacity of no more than about 0.5.

32. The composition of claim 1, further comprising at least one additive selected from the group consisting of fluoride sources, other fillers, pyrogenic fillers, whitening agents, anticaries agents, remineralizing agents, enzymes, breath fresheners, anesthetics, clotting agents, acid neutralizers, chemotherapeutic agents, immune response modifiers, medicaments, indicators, dyes, pigments, wetting agents, tartaric acid, chelating agents, surfactants, buffering agents, viscosity modifiers, thixotropes, polyols, antimicrobial agents, anti-inflammatory agents, antifungal agents, stabilizers, agents for treating xerostomia, desensitizers, and combinations thereof.

33. The composition of claim 4, wherein the composition is selected from the group consisting of dental restoratives, dental adhesives, dental cements, cavity liners, orthodontic adhesives, dental sealants, and dental coatings.

34. The composition of claim 4, wherein the composition comprises a multi-part composition comprising a first part and a second part, wherein each part can independently be selected from the group consisting of a liquid, paste, gel, or powder.

35. The composition of claim 1, wherein the combined mixture is in an unhardened state.

36. The composition of claim 1, wherein the combined mixture is in a hardened state.

37. A method of preparing a dental article said method comprising the steps of:
   (a) providing a dental composition of claim 1; and
   (b) hardening the dental composition to form the dental article.

38. The composition of claim 37, wherein the dental article is selected from the group consisting of dental mill blanks, dental crowns, dental fillings, dental prostheses, and orthodontic devices.

39. A multi-part hardenable dental composition comprising:
   (a) a first part comprising a polyacid;
   (b) a second part comprising an acid-reactive filler;
   (c) a nanofiller present in either or both parts;
   (d) water present in either or both parts; and
   (e) an optional polymerizable component present in either or both parts;
wherein the refractive index of a combined mixture of the polyacid, the nanofiller, the water, and the optional polymerizable component is within 4 percent of the refractive index of the acid-reactive filler.

40. The composition of claim 39, wherein the first part comprises a paste.

41. The composition of claim 39, wherein the second part comprises a paste.

42. The composition of claim 39, wherein the first part and the second part each comprises a paste.

* * * * *

UNITED STATES PATENT AND TRADEMARK OFFICE
CERTIFICATE OF CORRECTION

PATENT NO. : 7,090,721 B2
APPLICATION NO. : 10/847803
DATED : August 15, 2006
INVENTOR(S) : Bradley D. Craig It is certified that error appears in the above-identified patent and that said Letters Patent is hereby corrected as shown below:

On the title page item (56),
First Page, Column 2:
Line 29, After "6,376,590" delete "B1" and insert -- B2 --, therefor.

On the title page item (56),
Page 2, Column 1:
Line 8, After "6,693,143" delete "B1" and insert -- B2 --, therefor.
Line 10, After "6,696,507" delete "B1" and insert -- B2 --, therefor.

On the title page item (56), Other Publications,
Page 2, Column 2:
Line 2, Delete "filed" and insert -- filed on --, therefor.
Line 5, Delete "filed" and insert -- filed on --, therefor.
Line 7, Delete "filed" and insert -- filed on --, therefor.
Line 9, Delete "filed" and insert -- filed on --, therefor.
Line 11, Delete "Methods,"filed" and insert -- Methods,"filed on --, therefor.
Line 12, Delete "et al" and insert -- et al. --, therefor.
Line 15, Delete "(XP002331214" and insert -- (2002-07 XP002331214 --, therefor.
Line 16-17, Delete "new York" and insert -- New York --, therefor.
Line 17, Delete "Jul. 2002," and insert -- Jul. 2002 (2002-07), --, therefor.
Line 21, Delete "Noth-Holland" and insert -- North-Holland --, therefor.

Column 21:
Line 45, Delete "glass" and insert -- Glass --, therefor.
Line 47, Delete "Run5" and insert -- Run 5 --, therefor.

UNITED STATES PATENT AND TRADEMARK OFFICE
CERTIFICATE OF CORRECTION

PATENT NO. : 7,090,721 B2
APPLICATION NO. : 10/847803
DATED : August 15, 2006
INVENTOR(S) : Bradley D. Craig It is certified that error appears in the above-identified patent and that said Letters Patent is hereby corrected as shown below:

Column 27:
Line 33, Delete "Past A" and insert -- Paste A --, therefor.

Signed and Sealed this

Fifteenth Day of May, 2007

JON W. DUDAS
*Director of the United States Patent and Trademark Office*